United States Patent [19]

Koenig et al.

[11] Patent Number: 5,376,648
[45] Date of Patent: Dec. 27, 1994

[54] DERIVATIVES OF 4-(HETERO)ARYLMETHYLOXY PHENYL DIAZOLE, A METHOD OF PREPARING THEM AND USE THEREOF IN THERAPY

[75] Inventors: Jean-Jacques Koenig, Maisons Laffitte; Luc L. Lebreton, Dijon; Maryse F. Masson, Paris, all of France

[73] Assignee: Delalande S.A., Courberoie, France

[21] Appl. No.: 119,701

[22] Filed: Sep. 10, 1993

Related U.S. Application Data

[62] Division of Ser. No. 878,557, May 5, 1992, Pat. No. 5,262,432.

[30] Foreign Application Priority Data

Nov. 24, 1989 [FR] France ................... 89 15499

[51] Int. Cl.$^5$ .................... C07D 273/02; A61K 31/41
[52] U.S. Cl. ......................... 514/92; 548/144
[58] Field of Search ............... 548/144; 514/92

Primary Examiner—David B. Springer
Attorney, Agent, or Firm—Lappin & Kusmer

[57] ABSTRACT

Derivatives having the formula:

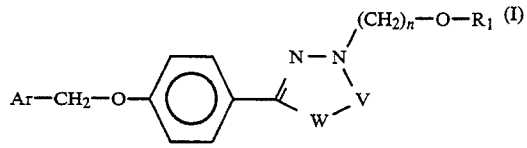

in which $R_1 = C_1-C_4$ alkyl and Ar is an aryl or heteroaryl group chosen from among the following:

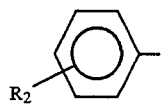

(i)

where $R_2$ represents a hydrogen atom one or two halogen atoms, a CN, $NO_2$ or $CF_3$ group, one, two or three $C_1-C_4$ alkyl or $C_1-C_4$ alkoxy groups or an amino group substituted by two $C_1-C_4$ alkyl groups, in which case the —W—V— chain represents —N=N— or

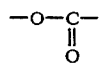

and n=2-6;
(ii) pyridyl, in which case the —W—V— chain represents —N=N— and n=1-6, and acid addition salts of those derivatives (I) which are salt-forming.

These derivatives are of use in therapy as agents for inhibiting type B monoamine oxydase.

8 Claims, No Drawings

DERIVATIVES OF 4-(HETERO)ARYLMETHYLOXY PHENYL DIAZOLE, A METHOD OF PREPARING THEM AND USE THEREOF IN THERAPY

This application is a divisional of U.S. Ser. No. 07/878,557, filed May 5, 1992, now U.S. Pat. No. 5,262,432.

The invention relates to new derivatives of 4-(hetero) arylmethyloxy phenyl diazole, a method of preparing them and use thereof in therapy.

More precisely, the derivatives according to the invention have the formula:

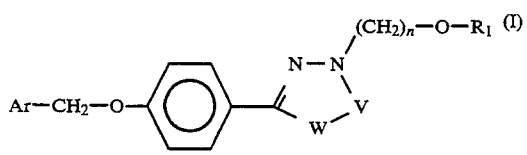

in which $R_1$ denotes $C_1$-$C_4$ alkyl and Ar is an aryl or heteroaryl group chosen from among the following:

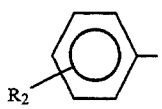

where $R_2$ represents a hydrogen atom, one or two halogen atoms, a CN, $NO_2$ or $CF_3$ group, one, two or three $C_1$-$C_4$ alkyl or $C_1$-$C_4$ alkoxy groups or an amino group substituted by two $C_1$-$C_4$ alkyl groups, in which case the —W—V— chain represents —N=N— or

and n=2-6;

(ii) pyridyl, in which case the —W—V-13 chain represents —N=N— and n=1-6.

Hereinbefore and hereinafter, the expression "$C_1$-$C_4$ alkyl" denotes straight-chain or branched hydrocarbon groups containing 1 to 4 carbon atoms, i.e. methyl, ethyl, n-propyl, i-propyl, n-butyl, i-butyl, sec.-butyl or tert-butyl; the expression "$C_1$-$C_4$ alkoxy" has the formula O—($C_1$-$C_4$ alkyl); the term halogen denotes fluorine, chlorine bromine or iodine; and the term pyridyl denotes 4-pyridyl, 3-pyridyl or 2-pyridyl.

The invention also relates to addition salts of a mineral acid (e.g. hydrochloric or sulphuric acid) or an organic acid (e.g. acetic, oxalic, maleic or tartric) of those derivatives (I) which are salt-forming.

The invention also covers a method of preparing the derivatives (I), the method comprising:

(a) condensation of compounds having the formula:

where n=2-6, $R_1$=$C_1$-$C_4$ alkyl and X denotes a good leaving. group such as a halogen atom (chlorine, bromine or iodine) or a mesyloxy or tosyloxy group, on to respective compounds having the formula:

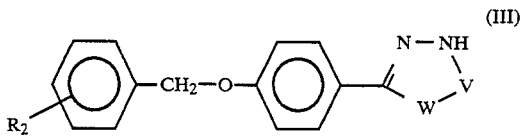

where —W—V— denotes —N=N— or

and $R_2$ has the same meaning as in formula (I), in the presence of a base such as a metal hydride, inter alia sodium hydride, in an aprotic anhydrous solvent such as dimethyl formamide;

(b) condensation of compounds having the formula:

where Ar has the same meaning as in formula (I) and X has the same meaning as in formula (II), on to respective compounds having the formula:

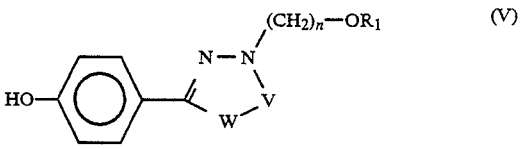

where $R_1$ and n have the same meanings as in formula (I) and —W—V— represents either —N=N— or

when Ar in formula (IV) is a phenyl ring substituted by $R_2$, the latter having the same meaning as in formula (I), or —N=N— when Ar in formula (IV) represents pyridyl, in the presence of a base such as $K_2CO_3$ or a metal hydride such as sodium hydride, in an anhydrous solvent such as DMF or acetonitrile;

(c) condensation of compounds having the formula:

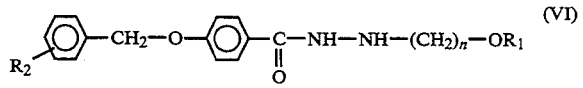

where n, $R_1$ and $R_2$ have the same meaning as in formula (I), with phosgene in an aprotic solvent such as dioxane, chloroform or toluene, for the purpose of cyclisation of the , 0053 chain of the compounds (VI) into

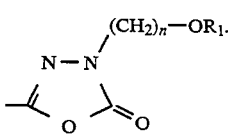

The formula (V) compounds can be obtained by debenzylation in the presence of hydrogen and a catalyst such as palladium on carbon, of the respective formula (I) compounds having the special structure:

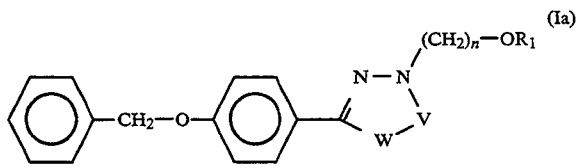

where —W—V—, $R_1$ and n have the same meaning as in formula (I), preferably in an alcoholic solvent such as ethanol or methanol.

The formula (III) compounds having the special structure:

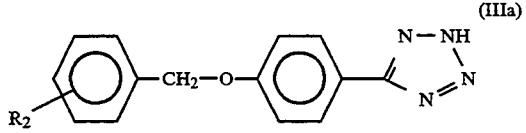

where $R_2$ has the same meaning as in formula (I), can be obtained by action of sodium azide on compounds having the formula:

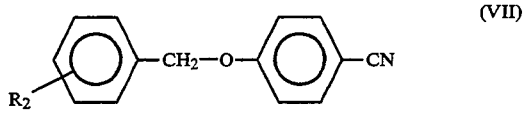

where $R_2$ has the same meaning as in formula (I), preferably by the method of R. M. HERBST described in J. Org. Chem. 22, 1142, 1957.

The formula (VII) compounds are obtained by treating the compound having the formula:

with a metal hydride such as sodium hydride in an aprotic solvent such as DMF and by reacting the resulting compound with formula (IV) compounds in which. Ar=

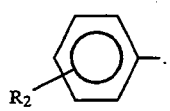

The formula (III) compounds having the special structure

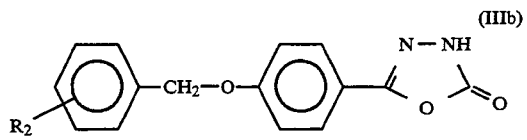

where $R_2$ has the same meaning as in formula (I), can be obtained by the method of FREUND and GOLDSMITH described in Ber. 21, 1240, 1882, by using hydrazides having the formula:

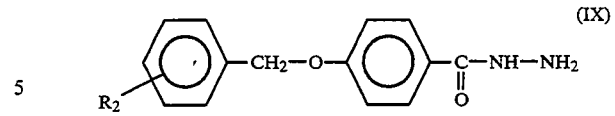

where $R_2$ has the same meaning as in formula (I).

The formula (IX) compounds can be obtained by action of hydrazine respectively on the ethyl or methyl ester of acids having the formula:

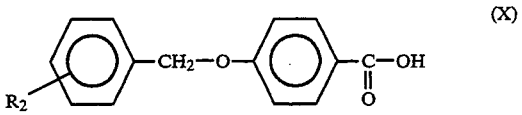

where $R_2$ has the same meaning as in formula (I), in an alcoholic medium, preferably ethanol.

The formula (VI) compounds are obtained by action of the methyl or ethyl ester of acids of formula (X) in an alcoholic medium such as ethanol or methanol, on the respective compounds having the formula:

$$NH_2-NH-(CH_2)_n-OR_1 \qquad (XI)$$

where n and $R_1$ have the same meaning as in formula (I), the last-mentioned compounds being obtained preferably by the method described in CA 63:9962.

The acid addition salts of the salt-forming derivatives of formula (I) can be obtained in conventional manner by action of an inorganic or organic acid on the salt-forming derivatives of formula (I), the acids and derivatives preferably being used in the form of miscible solutions.

The following preparations are given by way of example in order to illustrate the invention:

EXAMPLE 1

5-(4-benzyloxy phenyl) 2-methoxyethyl 2H tetrazole [(I); n=2, $R_1$=CH$_3$, —W—V—:—N=N—, Ar=phenyl] Code No: MD 230300

1st Step: 4-Benzyloxy Benzonitrile (VII)

$5.10^{-2}$ mol of NaH was added little by little to a solution of $5.10^{-2}$ mol of 4-hydroxy benzonitrile in 100 ml DMF so as to obtain a temperature of 25° C. The solution was then heated to 50° C. until No more hydrogen was liberated. After cooling to 0° C., $5.10^{-2}$ benzyl chloride was added. The reaction mixture was heated to 40° C. for 1 hour, then poured into 300 ml iced water. The resulting solid was separated by filtration.

2nd Step: 5-(4-Benzyloxy Phenyl) Tetrazole [(IIIa); $R_2$=H]

$6.6 \times 10^{-2}$ mol of sodium azide and $6.6 \times 10^{-2}$ mol of acetic acid were added to a solution of $5 \times 10^{-2}$ mol of 4-benzyloxy benzonitrile (VIII) in 20 ml butanol. The reaction medium was then reflux-heated for 4 hours. 1 g sodium azide, 2 g acetic acid and 10 ml butanol were added and the reaction medium was again reflux-heated for 2 days. After concentration by evaporation of the solvent, the residue was dissolved in 20 ml of 10% aqueous NaOH. After filtration, the aqueous phase was extracted with ether. The alkaline solution was acidified with 2N HCl to obtain the expected compound, which was isolated with an 85% yield (M.P.=228° C.).

3rd Step: 5-(4-Benzyloxy Phenyl) 2-Methoxyethyl 2H Tetrazole (I)

$2 \times 10^{-2}$ mol of the compound obtained in the second step was added to a solution of $2 \times 10^{-2}$ mol of sodium hydride in 50 ml DMF and the reaction medium was heated to 60°-80° C. until no more gas was evolved. After cooling, $2 \times 10^{-2}$ mol of 2-chloro-1-methoxyethane was added little by little. The reaction medium was heated to 80° C. for 12 hours, then concentrated to two-thirds and poured on to iced water. After extraction with ether, the expected product was obtained with a 48% yield.

M.P.=96° C. IR (KBr, $\nu$ cm$^{-1}$): 1610, 1450 $^1$H NMR ($\delta$ ppm, DMSOd6): 3.2 (3H); 3.9 (2H); 5.3 (2H); 7.2 (2H); 7.4 (5H); 8 (2H).

The other formula (I) derivatives in which Ar=

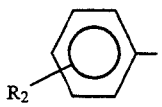

can be obtained in the same manner, inter alia the following:

5-[4-(4-chlorobenzyloxy) phenyl]2-methoxyethyl 2H-tetrazole

[(I); —W—V—:—N=N—, $R_1$=CH$_3$, n=2, Ar=4-chloro phenyl] Code No: MD 230305

Yield=44% M.P.=90° C. IR (KBr, $\nu$ cm$^1$); 1620, 1420, 1410, 1210 $^1$H NMR ($\delta$ ppm, DMSOd6): 3.2 (3H); 3.9 (2H); 4.9 (2H); 5.2 (2H); 7.2 (2H); 7.5 (4H); 8 (2H);

5-[4-(3-chlorobenzyloxy) phenyl]2-methoxyethyl 2H tetrazole

[(I) :—W—V—:—N=N—, $R_1$=CH$_3$, n=2, Ar=3-chloro phenyl Code No: MD 230324

M.P.=92° C. $^1$H NMR ($\delta$ ppm, DMSOd6): 3,4 (3H); 4 (2H); 4.8 (2H); 5.1 (2H); 7 (2H); 7.3 (4H); 8 (2H).

EXAMPLE 2

5-[4-(4-chlorobenzyloxy) phenyl ]3-methoxyethyl 3H-1, 3,4 oxadiazol 2-one (I) :

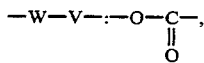

$R_1$=CH$_3$, n=2, Ar=4-chloro phenyl ] Code No: MD 230306

1st Step: 1-[4-(4-Chlorobenzyloxy) Benzoyl] Hydrazine (IX)

2.75 mol of hydrazine hydrate was added to a solution of 0.275 mol of ethyl ester of 4-(4-chloro benzyloxy) benzoic acid (X) in 300 ml ethanol. The reaction medium was reflux-heated for 48 hours. After cooling, the expected product was separated by filtration and recrystallised from ethanol.

Yield=63% M.P.=168° C.

2nd Step: 5-[4-(4-Chlorobenzyloxy) Phenyl] 3H 1,3,4-Oxadiazol 2-one (IIIb)

A solution of 0.0723 mol of phosgene in 5 ml toluene was added to a solution of 0.0723 mol of the compound obtained in the preceding step in 200 ml toluene. The mixture was agitated at ambient temperature for 18 hours. After filtration, the substance obtained was recrystallised from butanol.

Yield=78% M.P.=236° C.

3rd Step: 5-[4-(4-Chlorobenzyloxy) Phenyl] 3-Methoxyethyl 3H 1,3,4-oxadiazol-2-one (I)

0,016 mol of NaH was added to a solution of 0.016 mol of the compound obtained in the preceding step in 50 ml DMF, followed by heating to 60°-80° C. until no more hydrogen was evolved. After cooling, 0.016 mol of 2-chloro 1-methoxy ethane was added dropwise, and then the reaction medium was heated to 80° C. for 12 hours, then concentrated to two-thirds and poured, on to iced water.

The expected product was obtained by extraction with ether, with a 36% yield.

M.P.=140° C. IR (KBr, $\nu$ cm$^{-1}$) : 1780, 1610, 1245, 1115, 1000. $^1$H NMR (DMSOd6) $\delta$ ppm: 3.2 (3H); −3.8 (4H); 5.2 (2H); 7.2 (2H); 7.5 (4H); 7.7 (2H).

EXAMPLE 3

2-methoxyethyl 5-[4-(4-pyridyl methyloxy) phenyl ]2H tetrazole hydrochloride [(I); —W—V—:—N=N—, n=2, $R_1$=CH$_3$, Ar=4-pyridyl] Code No: MD 230307

1st Step: 5-(4-Hydroxyphenyl) 2-Methoxyethyl 2H Tetrazole [(V); —W—V—:—N=N—, n=2, $R_1$=CH$_3$]

0.04 g of 10% palladium on carbon moistened to 50% was added to a solution of $0.6 \times 10^{-3}$ mol of compound MD 230300 in 20 ml of a mixture of methanol and methylene chloride (50-50) and a stream of hydrogen was supplied at normal pressure for 3 hours. After filtration and concentration, the resulting substance was recystallised from a mixture of ethyl ether and petroleum ether.

Yield=75% M.P.=110° C.

2nd Step: 2-Methoxyethyl 5-[4-(4-Pyridyl Methyloxy) Phenyl ]2H Tetrazole Hydrochloride (I)

0.0567 mol of $K_2CO_3$ and 0.0227 mol of 4-chloromethyl pyridine were added to a solution of 0.0227 mol of the compound obtained in the preceding step in 100 ml acetonitrile. The reaction medium was reflux-heated for 48 hours, then concentrated and dissolved in a 0.1N solution of NaOH. After extraction with methylene chloride, the organic phase was dried on sodium sulphate and concentrated. The resulting base was dissolved in ethanol, followed by addition of hydrochloric ethanol. The expected hydrochloride precipitated and was recrystallised from ethanol.

Yield=15% M.P.=190° C. IR (KBr, $\nu$ cm$^{-1}$) : 2400, 2100, 2000, 1640, 1615, 1470, 1260, 1250, 1120 $^1$H NMR ($\delta$ ppm, DMSOd6): 3.2 (3H); 3.9 (2H); 4.9 (2H); 5.6 (2H); 7.2 (2H); 8 (4H); 8.9 (2H); 7.7 (1H exchangeable).

The other derivatives (I) are obtained in the same manner, inter alia 2-(methoxyethyl) 5-[4-(3-pyridyl methyloxy)phenyl] 2H tetrazole [(I); —W—V—:—N=N—, n=2, $R_1$=CH$_3$, Ar=3-pyridyl]. Code No: MD 230308.

M.P.=160° C. IR (KBr, $\nu$ cm$^{-1}$): 2550, 2100, 1615, 1550, 1420, 1405, 1260 $^1$H NMR ($\delta$ ppm, DMSOd6): 3.3 (3H); 4 (2H); 4.95 (2H); 5.5 (2H); 7.3 (2H); 8 (3H); 8.5–8.9 (3H); 9.1 (1H exch).

The formula (I) derivatives and their pharmaceutically acceptable acid addition salts have been studied in laboratory animals and have shown pharmacological activity, inter alia selective activity for inhibiting type B monoamine oxidase (MAO-B).

The activity of the Compounds in inhibiting monoamine oxidase was shown by measurements of MAO in vitro.

The MAO activity was determined, using a mitochondrial suspension of rat brain as a source of enzyme. The standard method of determination consists in pre-incubating the enzyme for 20 minutes, first in the absence and then in the presence of the inhibitors. The activities were determined by using serotonin (5 HT) and phenethylamine (PEA) as substrates of MAO-A and MAO-B, the reaction time being 40 minutes with 5 HT and 10 minutes with PEA. The method of operation used was that of P.C. Baker: Dev. Biol. 14, 267, 1966.

The activities of a number of compounds according to the invention as against MAO-B and MAO-A are given via their inhibition constants Ki(MAO-B) and Ki(MAO-A) and are shown in the following Table.

TABLE

| Compound tested Code Number | Ki (MAO-B) | Ki (MAO-A) |
| --- | --- | --- |
| MD 230300 | $1.56 \times 10^{-8}$ M/L | inactive |
| MD 230305 | $1.84 \times 10^{-7}$ M/L | inactive |
| MD 230306 | $5 \times 10^{-9}$ M/L | inactive |
| MD 230324 | $3.5 \times 10^{-8}$ M/L | inactive |

With regard to the toxicity of the formula (I) derivatives and their pharmaceutically acceptable acid addition salts, after oral administration to the mouse, no toxicity was observed for 24 hours, up to a dose of 1500 mg/kg.

The formula (I) derivatives and their pharmaceutically acceptable acid addition salts can be used for preparation of drugs for inhibiting type B monoamine oxidase. These drugs are of use in therapy, inter alia for treatment of neurological disturbances connected with pathological ageing, disturbances of memory, mood, schizophrenia, psychasthenia or psychic slowing-down due to ageing, certain forms of depression and Parkinson's disease.

The drugs can be administered to man or any warm-blooded animal in various pharmaceutical forms well known in the art, inter alia in the form of compounds formulated for oral, parenteral or rectal administration.

For oral administration, the compositions can be in the form of pills, dragees or capsules, prepared by conventional methods using known supports and excipients such as binders, fillers, lubricants and disintegrating agents; they may also take the form of solutions, syrup or suspensions.

For parenteral administration, the compositions according to the invention can be in the form of injectable solutions, suspensions or emulsions comprising a parenterally acceptable, oily or aqueous liquid vehicle.

For rectal administration, the compositions can be in the form of suppositories containing conventional bases for suppositories.

The amount of the active principles, i.e. derivatives (I) and their pharmaceutically acceptable acid addition salts, which can be administered depends inter alia on the way of administration, the body weight of the patient and the therapeutic power of the compounds used. The amount orally administered may generally be up to 50 mg/kg of active principle per day (in one or two doses); the amounts for parenteral administration may be up to 5 mg/kg of active principle per day (in one or more doses); and the amounts for rectal administration may be up to 10 mg/kg of active principle per day (in one or two suppositories).

We claim:

1. Compounds having the formula:

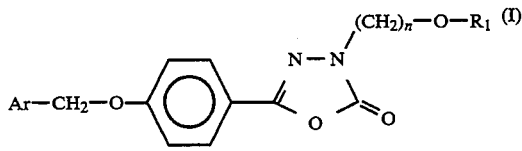

in which $R_1$ denotes $C_1$-$C_4$ alkyl, n is 2 to 6 and Ar is a group of formula:

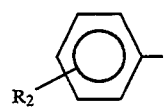

where $R_2$ represents a hydrogen atom, one or two halogen atoms, a CN, $NO_2$ or $CF_3$ group, one, two or three $C_1$-$C_4$ alkyl or $C_1$-$C_4$ alkoxy groups, or an amino group substituted by two $C_1$-$C_4$ alkyl groups and the pharmaceutically acceptable acid addition salts thereof.

2. A compound consisting essentially of 5-[4-(4-chloro benzyloxy)phenyl] 3-methoxyethyl 3H-1,3,4-oxadiazol-2-one.

3. A pharmaceutical composition consisting essentially of a compound or salt according to any of claims 1 and 2 mixed with a pharmaceutically acceptable excipient.

4. Compounds according to claim 1, wherein said acid addition salts are selected from the group consisting of mineral acid salts and organic acid salts.

5. Compounds according to claim 1, wherein said acid addition salts are mineral acid salts selected from the group consisting of hydrochloric and sulfuric acid salts.

6. Compounds according to claim 1, wherein said acid addition salts are organic acid salts selected from the group consisting of acetic, oxalic, maleic and tartric acid salts.

7. A method for inhibiting type B monoamine oxidase in man or warm-blooded animal, which consists in internally administering thereto a type B monoamine oxidase inhibiting effective amount of a compound having the formula:

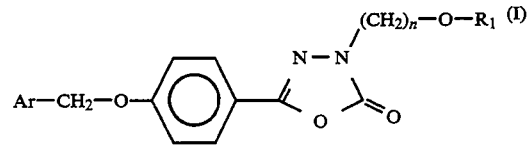

in which $R_1$ denotes $C_1$-$C_4$ alkyl, n is 2 to 6 and Ar is a group of formula:

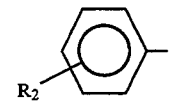

where $R_2$ represents a hydrogen atom, one or two halogen atoms, a CN, $NO_2$ or $CF_3$ group, one, two or three $C_1$-$C_4$ alkyl or $C_1$-$C_4$ alkoxy groups or an amino group substituted by two $C_1$–$C_4$ alkyl groups, or of a pharmaceutically acceptable acid addition salt thereof.

8. Method of treating human or warm-blooded animals for neurological disturbances connected with pathological aging, disturbances of memory, mood, schizophrenia, psychasthenia, psychic slowing-down due to aging, certain forms of depression or Parkinson's disease comprising administering a type B monoamino oxidase inhibiting effective amount of a compound having the formula:

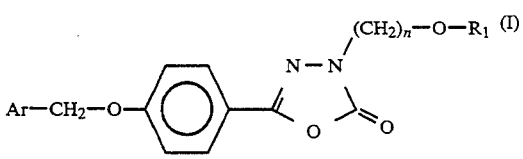

in which $R_1$ denotes $C_1$–$C_4$ alkyl, n is 2 to 6 and Ar is a group of formula:

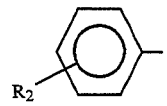

where $R_2$ represents a hydrogen atom, one or two halogen atoms, a CN, $NO_2$ or $CF_3$ group, one, two or three $C_1$–$C_4$ alkyl or $C_1$–$C_4$ alkoxy groups or an amino group substituted by two $C_1$–$C_4$ alkyl groups, or of a pharmaceutically acceptable acid addition salt thereof.

* * * * *